United States Patent [19]

Kammann, Jr. et al.

[11] Patent Number: 4,485,044

[45] Date of Patent: Nov. 27, 1984

[54] SULFURIZED ESTERS OF POLYCARBOXYLIC ACIDS

[75] Inventors: Karl P. Kammann, Jr., Crown Point; Paul F. Thompson, Munster, both of Ind.

[73] Assignee: Ferro Corporation, Cleveland, Ohio

[21] Appl. No.: 351,842

[22] Filed: Feb. 24, 1982

[51] Int. Cl.$^3$ .............................................. C08H 3/00
[52] U.S. Cl. ....................................... 260/399; 44/66; 252/48.6
[58] Field of Search ........................................ 260/399

[56] References Cited

U.S. PATENT DOCUMENTS

| | | | |
|---|---|---|---|
| 2,137,584 | 11/1938 | Ott .................................. | 260/399 X |
| 2,371,207 | 3/1945 | Zublin et al. .................... | 260/399 X |
| 2,372,366 | 3/1945 | DeGroote et al. ................ | 260/399 |
| 2,372,641 | 4/1945 | Allen ................................ | 260/399 |
| 2,373,015 | 4/1945 | Cowan et al. ..................... | 260/399 |
| 2,384,443 | 9/1945 | Cowan et al. .................... | 260/399 X |
| 2,415,838 | 2/1947 | Musselman et al. ............. | 260/399 X |
| 2,605,193 | 7/1952 | Karll ................................. | 260/399 X |
| 2,628,939 | 2/1953 | Blake ................................ | 260/399 X |
| 2,800,500 | 7/1957 | Matuszak et al. ................ | 260/399 X |
| 4,152,278 | 5/1979 | Bell .................................. | 260/399 X |
| 4,380,498 | 4/1983 | Kammann, Jr. et al. ......... | 260/399 X |
| 4,380,499 | 4/1983 | Kammann, Jr. et al. ......... | 260/399 X |

Primary Examiner—Thomas A. Waltz
Attorney, Agent, or Firm—Philip Hill; Milton L. Simmons

[57] ABSTRACT

Improved additive compositions comprise sulfurized, esterified, unsaturated polycarboxylic acids. Such additive compositions possess good solubility in oils and impart improved lubrication and anti-oxidant properties to lubricant, fuel, and metal-working compositions.

5 Claims, No Drawings

SULFURIZED ESTERS OF POLYCARBOXYLIC ACIDS

BACKGROUND OF THE INVENTION

It has been common practice to include in lubricant formulations additives to provide improved antiwear and rust inhibition properties. In the past, sulfurized triglycerides, such as sulfurized lard oil, have been utilized, especially in association with lightly refined aromatic mineral oils which provided sufficient solubility for the sulfurized triglycerides.

With the increased concern for toxicity of aromatic compounds found in such mineral oils, lubricant formulations now comprise essentially non-aromatic oils. This change to substantially non-aromatic base oils created a major problem, resulting from a significant decrease in solubility of the sulfurized triglycerides in the non-aromatic mineral oil, resulting in solidification and/or dropout of the sulfurized triglycerides.

While the solubility problem has been overcome, the modified lubricant products have been found to be either deficient in desirable lubricant properties or incapable of providing needed improvement in these properties.

In a typical approach to this problem, as reported in U.S. Pat. No. 3,455,896, sulfurized, low molecular weight polybutenes were reacted with liquid triglycerides, which were susceptible of sulfurization, to yield an additive. In U.S. Pat. No. 3,850,825, another additive was prepared by the sulfurization of a mixture of prime burning lard oil and alkyl oleate. In U.S. Pat. No. 3,740,333, $C_{10}$–$C_{16}$ alcohol esters of unsaturated fatty acids, having 18 to 22 carbon atoms, were blended with a triglyceride and either used "as is" or sulfurized. Modifications of such compositions have been reported in U.S. Pat. Nos. 4,149,982, 4,166,795, 4,166,796, 4,166,797 and 4,188,300. Esters of polymer acids have been employed as additives for metal-working aqueous dispersants and as fuel lubricant additives in, respectively, U.S. Pat. Nos. 4,067,817 and 4,167,486.

The triglyceride compositions of the prior art, typically derived from plants and animals, have not provided maximum effectiveness as lubricant additives because of the chain length and/or the degree of unsaturation of the acid moiety. Modification of said acid moieties of the triglycerides, as by transesterification, have produced novel triglycerides and have improved the properties of the resulting additive when said novel triglycerides were coupled, through sulfur bonds, with solubilizing components, such as esters and/or olefins.

Although these prior art efforts have increased the solubility of sulfurized fatty oils to acceptable values, there has remained a serious need for sulfurized additives possessing both good solubility and a combination of improved lubricant properties, such as, for example, better low temperature flow properties, better load carrying and antifriction properties, and better anti-oxidant properties, leading to less sludging and gumming. Such improved lubricant properties would also be attractive for use in various fuels systems employed for power generation and heating purposes.

SUMMARY OF THE INVENTION

This invention relates to improved additive compositions comprising sulfurized ester oils, to the process for their preparation, and to oil product compositions, including fuels, lubricants, and metal-working compositions, incorporating such sulfurized oils. The additive compositions of this invention exhibit highly desirable solubility properties when employed in either lubricant or fuel formulations. The particularly desirable utility of these additive compositions derives from their providing generally improved performance characteristics, ranging from improved load carrying, antiwear, and friction properties, to reduced levels of deposits and varnish, and to improved pour-point depression.

This invention particularly relates to sulfurized, ester compositions, comprising one or more sulfurized esters of unsaturated polybasic carboxylic acids, wherein such acids have at least two carboxyl groups.

This invention further relates to the method for preparation of such sulfurized ester compositions.

This invention additionally relates to lubricant and fuel compositions incorporating such sulfurized ester compositions, whereby improved performance in conventional usages is achieved. The additives of this invention may be employed in concentrations up to about 15 wt. % in lubricant formulations and up to about 0.3 wt. % in fuel compositions.

DESCRIPTION OF THE INVENTION

This invention is directed to additive compositions of sulfurized ester oils, and to the process of preparing said compositions, which exhibit the required solubility properties in non-aromatic base oils or in synthetic base oils without the disadvantages associated with the prior art lubricant additive formulations. In addition, the compositions of this invention exhibit improved performance characteristics, over the compositions of the prior art, including improved load carrying, antiwear, and friction properties, reduced levels of deposits and varnish in used oils, and better pour-point depression. This invention is likewise directed to lubricant, fuel, and metal-working formulations which include the inventive additive compositions.

The acid moiety of the additives of this invention consists of one or more organic acids, having two or more carboxylic acid groups, preferably comprising di- and/or tri-carboxylic acids. Particularly preferred are dimer acids of oleic acid, of linoleic acid or of acrylic and linoleic acids. Also particularly preferred are mixtures of the dimers and trimers of linoleic acid and/or of oleic acid. Generally, the acid moiety will have from about 21 to about 54 carbon atoms per molecule.

The alcohol moiety of the additives of this invention consists of monohydric, dihydric, and polyhydric alcohols, particularly those having 8 or more, up to about 22, carbon atoms per molecule, although alcohols having fewer carbon atoms per molecule are suitable.

Following esterification, employing selected acid and alcohol components, the ester products are coupled by reaction with sulfur in, where desired, the added presence of other components, such as natural triglycerides, esters, olefins or blends thereof. However, such solubilizing components are not absolutely required with the additives of this invention. The sulfurization is conducted in accordance with known procedures which generally consist of heating the mixture with elemental sulfur at temperatures from about 300° F. to about 400° F. for from about 1 to about 8 hours. The sulfur content of the additives of this invention should be within the range from about 1.0 to about 18 wt. %, preferably from about 1.5 to about 10 wt. %, and most preferably from about 2.0 to about 8.0 wt. %.

The following examples serve, without limitation, to describe the invention more fully as it relates to additive compositions. In the examples all parts and percentages are on a weight basis unless otherwise indicated.

EXAMPLE 1

A mixture of 382 g. (1.36 equiv.) commercial dimer acid, containing 73% dimerized oleic/linoleic acids, 24% trimerized oleic/linoleic acids, and 3% monomer acids, and 216 g. (1.37 equiv.) isodecyl alcohol was stirred at 350°–360° F. for 4 hours in the presence of 1 g. p-toluenesulfonic acid. The ester product was recovered by conventional means and had an acid value (A.V.) of 8. The acid value is determined by titration (A.O.C.S. method Cd 3a-63) and is defined as the number of milligrams of potassium hydroxide required to neutralize the free acids in one gram of sample.

The ester product I (191.6 g.) was heated, with stirring, to 290° F. and 8.4 g. sulfur was added. The mixture was then heated to 370°–380° F., maintained at that temperature for 2 hours, cooled to 250° F., and blown with air for 1.5 hours to remove hydrogen sulfide. The final product II contained 3.8 wt. % sulfur and was inactive to copper (A.S.T.M. D-130 test procedure).

EXAMPLE 2

The procedure of Example 1 was repeated employing substantially identical equivalent proportions of a second commercial dimer acid, together with isodecyl alcohol, to yield ester product III. After sulfurization as in Example 1, product IV contained 3.5 wt. % bound sulfur.

EXAMPLE 3

The procedure of Example 1 was repeated employing a commercial dibasic acid, comprising the addition product of acrylic acid and conjugated linoleic acid, together with isodecyl alcohol to yield ester product V. Sulfurized product VI contained 3.8 wt. % bound sulfur.

EXAMPLE 4

The procedure of Example 1 was repeated employing a commercial trimer acid, containing 10% dimerized linoleic/oleic acids and 90% trimerized linoleic/oleic acids, together with isodecyl acid to yield ester product VII. Sulfurized product VIII contained 2.2 wt. % bound sulfur.

EXAMPLE 5

The procedure of Example 1 was followed employing a commercial dimer acid, containing 60% dimerized linoleic/oleic acids, 25% trimerized linoleic/oleic acids, and 15% higher polycarboxylic acids, together with dodecanol, to yield ester product IX and sulfurized ester product X which contained 3.5 wt. % sulfur.

EXAMPLE 6

The procedure of Example 5 was repeated with substitution of a commercial diol concentrate, containing 18% $C_{15-16}$ monohydric alcohols and 82% $C_{13-17}$ dihydric alcohols, to yield ester product XI. After sulfurization, sulfurized ester product XII contained 3.5 wt. % bound sulfur.

EXAMPLE 7

The procedure of Example 1 was repeated employing a commercial dimer acid containing 75% dimerized linoleic/oleic acids, 22% trimerized linoleic/oleic acids, and 3% monomer acids, together with isodecyl alcohol, to yield ester product XIII and sulfurized ester product XIV which contained 5.5 wt. % bound sulfur.

EXAMPLE A

A mixture of 50% prime burning lard oil and 50% isodecyl alcohol ester of tall oil fatty acids was sulfurized to yield product A, containing 9.1 wt. % bound sulfur.

Products exemplary of the sulfurized ester additive compositions of this invention, prepared as described in Examples 1–7, above, together with comparison product A, were tested by conventional procedures.

The improved load carrying and friction reduction properties imparted by the use of the additives of the present invention are illustrated by the data in Table I, wherein the unsulfurized preparations illustrate the prior art, showing the improved load carrying and friction reduction (torque) of the novel additives as measured by the Falex step-up test. The lowest torque observed with any unsulfurized ester was higher than any torque observed with any of the sulfurized esters of this invention. Tests presented in Table I were conducted with a pour-depressed engine oil, 10W40 grade, Brand "B", having a pour point of −22° F.

Falex procedures for evaluating lubricants are described in Lubrication Engineering, 24, No. 8, 349–358 (1968). The procedure employed was as follows:

After a 5 minute warmup at 250 lbs., the load is increased in 250 lb. increments and held at each increment for one minute, until failure, which is of the weld type. Time at failure load before failure occurs is also noted. Torque comparisons were also made to show differences in friction.

Both sulfurized and unsulfurized dimer acid esters were tested for solubility in synthetic hydrocarbon oils. Each sample was dissolved (2 wt. %) in Gulf Synlube 4 cs with warming and stirring. After being maintained at 45° F. for four days, the solutions had the following appearances.

| Formulation | Appearance |
| --- | --- |
| Additive III (2 wt. %) | Clear |
| Additive IV (2 wt. %) | Clear |
| Product A (2 wt. %) | Slight dropout |

Additional Falex step-up tests were performed with non-formulated base oils, including a mineral oil and a synthetic lubricating oil base stock. As shown in Table II, the oil properties were improved in each case by use of the sulfurized additives of this invention.

In another illustration, crankcase oil, formulated to be a high quality SE Grade 10W40 crankcase oil, was evaluated using a four-ball machine in testing for friction and wear as described in the ASTM-D-2266 procedure. The crankcase oil alone was compared with crankcase oil containing 2% additive IV. Tests were conducted at 1800 R.P.M., using a 40 kg. load, for one hour at 350° F. The results obtained were as follows:

| Formulation | Wear-Scar Diameter | Coefficient of Friction |
| --- | --- | --- |
| Crankcase Oil | 0.986 mm. | 0.11 |
| Crankcase Oil + Additive IV | 0.83 mm. | 0.102 |

In a further illustration, several of the products of this invention, together with the prior art product from Example A, were dissolved in 10W40 grade engine oil, Brand "B", in the amount of 3 wt. % and held for 16 hours at −20° F. Although the concentration employed is somewhat greater than would normally be used, the results presented in Table III show that the sulfurized ester additive compositions of this invention do not interfere with the action of the pour depressants contained in the Brand "B" oil.

The pour depressancy effects of an unsulfurized ester and corresponding sulfurized ester of this invention on a mineral oil were determined. The pour point of a highly paraffinic mineral oil, viscosity 27 cst. at 40° C., was 5° F. When 2 wt. % of additive III was dissolved in the mineral oil, the pour point was −5° F. When 2 wt. % of additive IV (Sulfurized III) was dissolved in the mineral oil, the pour point was −10° F.

Several of the sulfurized ester products of this invention, and also the corresponding unsulfurized esters, were dissolved, in the amount of 2 wt. %, in a formulated crankcase oil. The oil was formulated to be a high quality SE Grade 10W40 crankcase oil, except without overbased calcium phenate, which is known to function as an oxidation inhibitor. The following oxidation stability tests show that the sulfurized products of this invention may be used in lubricating oils to enhance oxidation resistance and to reduce sludge and deposit formation when subjected to high temperatures in the presence of cast iron as is present in an engine block.

In these tests a cast iron plate with several 18 mm. diameter dimples was used. Into the dimples were placed 0.30 g. of various oil samples. The plate was put into a high temp. (260°–265° C.) forced air oven and withdrawn every 20 minutes, up to 100 min. total. Upon each withdrawal, a crop of each test solution was spotted on filter paper (Camag 25240). The oil/additive solution, if not severely oxidized, spread in a uniform circle. Upon severe oxidation, the applied material stayed as a small gummy spot. Comparisons were made at the various time intervals. For all the samples, oxidation increased consistently with time. At the conclusion, the test samples appeared as described below. The samples, except for those containing the three unsulfurized esters, which looked similar, are listed in decreasing order of oxidation.

| Additive | Identity | Appearance |
|---|---|---|
| None | — | Tacky, gummy |
| VII | Unsulfurized ester | Slight improvement over oil alone |
| III | Unsulfurized ester | Slight improvement over oil alone |
| XIII | Unsulfurized ester | Slight improvement over oil alone |
| VIII | Sulfurized VII (2.2% S) | Oil spreads somewhat |
| IV | Sulfurized III (3.5% S) | Oil spreads fairly well |
| XIV | Sulfurized XIII (5.5% S) | Oil spreads well |

The sulfurized ester additive compositions of this invention are effective when employed in lubricating oils at concentrations ranging from about 0.05 to about 15 wt. %. The preferred concentration range is generally from about 2 to about 6 wt. %.

In other embodiments of this invention the sulfurized ester additive compositions are effective in various types of fuels, particularly to improve the lubrication of fuel pumps; to reduce wear on pistons, rings, and cylinders; and to reduce deposit formation. Such fuels broadly include gasolines, for use in spark-ignition internal combustion engines; and heating (or furnace) oils, for use in oil-fired burner assemblies. Other advantages include, when employed in fuel oils or diesel fuels, reduction of pour points and attendant reduction in plugging of oil filters. In such novel and improved fuel compositions, the additives of this invention are effective at relatively low concentrations within the range from about 0.0005 to about 0.3 wt. %, and preferably from about 0.0015 to about 0.05 wt. %.

In still further embodiments of this invention the sulfurized ester additive compositions are effective in improving the performance characteristics of metal-working compositions such as cutting oils, grinding oils, and the like. In such novel and improved oil compositions, the additives of this invention are effective generally within the concentration range from about 1.0 to about 10 wt. %, and preferably from about 3.0 to about 5.0 wt. %.

TABLE I

| Falex Step-Up Test 2 wt. % Additive in 10W40 Oil, Brand "B" | | |
|---|---|---|
| | Lbs. Load Before Failure | Torque at 1500 lbs. |
| Oil alone | 1250 (10 sec.)* | (40 at 1250) |
| I | 1500 (5 sec.) | 31 |
| II | 1500 (20 sec.) | 28 |
| III | 1500 (30 sec.) | 29 |
| IV | 1750 (57 sec.) | 27.5 |
| V | 1500 (1 sec.) | 31 |
| VI | 1500 (45 sec.) | 28 |
| VII | 1500 (30 sec.) | 30 |
| VIII | 1750 (60 sec.) | 25 |
| IX | 1500 (15 sec.) | 33 |
| X | 1750 (5 sec.) | 28 |
| XI | 1750 (10 sec.) | 28.5 |
| XII | 1750 (50 sec.) | 27.5 |
| XIII | 1500 (5 sec.) | 30 |
| XIV | 1750 (20 sec.) | 28 |
| A | 1500 | 30 |

*Time at failure load before failure.

TABLE II

| Falex Step-Up Test 2 wt. % Additive in Non-Formulated Base Oil | | |
|---|---|---|
| | Lbs. Load Before Failure | Torque at 750 lbs. |
| Mid-Continent Oil | 750 (2 sec.)* | — |
| III | 750 (26 sec.) | 18.5 |
| IV | 1000 (30 sec.) | 16 |
| Gulf Synfluid 4cs | 250–500** | — |
| III | 1000 (10 sec.) | 15 |
| IV | 1250 (40 sec.) | 14 |

*Time at failure load before failure.
**Failed during step-up.

TABLE III

| Flow Properties 3 wt. % Additives in 10W40 Oil, Brand "B" | |
|---|---|
| | After 16 hrs. at −20° F. |
| Oil alone | Flows |
| II | Flows |
| III | Flows |
| VI | Flows |
| VIII | Flows |
| A | No Flow |

What is claimed is:

1. An additive composition, comprising one or more sulfurized esters of an unsaturated dibasic carboxylic acid, wherein:
   (a) the unsaturated dibasic carboxylic acid moiety of the unsaturated esters comprises the addition product of linoleic acid and acrylic acid;
   (b) the alcohol moiety of the unsaturated esters comprises a monohydric alcohol having from about 8 to about 22 carbon atoms per molecule; and
   (c) the sulfur moiety comprises bound sulfur, present in an amount from about 2.0 wt. % to about 8.0 wt. %, based on the sulfurized ester product, introduced into the unsaturated ester by heating with elemental sulfur at a temperature within the range from about 300° F. to about 400° F.

2. The additive composition of claim 1 wherein the monohydric alcohol is isodecyl alcohol.

3. The additive composition of claim 1 wherein the monohydric alcohol is dodecanol.

4. The additive composition of claim 1 wherein the sulfurization is effected by heating the unsaturated ester with elemental sulfur for from about 1 to about 8 hours, followed by blowing with air to remove hydrogen sulfide.

5. The additive composition of claim 1 wherein the sulfurization of the unsaturated esters is effected in the presence of an added solubilizing component selected from the class consisting of natural triglycerides, esters, olefins, and blends thereof.

* * * * *